(12) United States Patent
Jang et al.

(10) Patent No.: US 11,426,130 B2
(45) Date of Patent: Aug. 30, 2022

(54) APPARATUS AND METHOD FOR ESTIMATING BLOOD PRESSURE

(71) Applicant: SAMSUNG ELECTRONICS CO., LTD., Suwon-si (KR)

(72) Inventors: Dae Geun Jang, Yongin-si (KR); Ui Kun Kwon, Hwaseong-si (KR); Chang Soon Park, Chungju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 481 days.

(21) Appl. No.: 16/414,446

(22) Filed: May 16, 2019

(65) Prior Publication Data

US 2020/0054290 A1 Feb. 20, 2020

(30) Foreign Application Priority Data

Aug. 20, 2018 (KR) .................. 10-2018-0096674

(51) Int. Cl.
| | |
|---|---|
| *A61B 5/021* | (2006.01) |
| *A61B 5/024* | (2006.01) |
| *A61B 5/029* | (2006.01) |
| *A61B 5/318* | (2021.01) |
| *A61B 5/389* | (2021.01) |
| *A61B 5/00* | (2006.01) |
| *A61B 5/11* | (2006.01) |

(52) U.S. Cl.
CPC ............ *A61B 5/7278* (2013.01); *A61B 5/029* (2013.01); *A61B 5/02116* (2013.01); *A61B 5/02125* (2013.01); *A61B 5/1102* (2013.01); *A61B 5/318* (2021.01); *A61B 5/389* (2021.01); *A61B 5/02416* (2013.01); *A61B 2560/0223* (2013.01)

(58) Field of Classification Search
CPC .............. A61B 5/7278; A61B 5/02116; A61B 5/02125; A61B 5/029; A61B 5/1102; A61B 5/318; A61B 5/389; A61B 5/02416; A61B 2560/0223; A61B 5/021; A61B 5/0022; A61B 5/7235; A61B 5/7275
See application file for complete search history.

(56) References Cited

U.S. PATENT DOCUMENTS

| | | | |
|---|---|---|---|
| 7,479,111 B2 | 1/2009 | Zhang et al. | |
| 8,706,464 B2 | 4/2014 | Shusterman | |
| 8,715,193 B2 | 5/2014 | Takala et al. | |
| 8,968,207 B2 | 3/2015 | Cohen | |

(Continued)

FOREIGN PATENT DOCUMENTS

| | | |
|---|---|---|
| JP | 2005-312947 A | 11/2005 |
| JP | 2015-198740 A | 11/2015 |

(Continued)

*Primary Examiner* — Navin Natnithithadha
(74) *Attorney, Agent, or Firm* — Sughrue Mion, PLLC

(57) ABSTRACT

An apparatus for non-invasively estimating blood pressure is provided. According to one embodiment, the apparatus for estimating blood pressure may include a bio-signal sensor configured to measure a bio-signal from a user and a processor configured to extract a feature from the bio-signal at an extraction time, acquire an offset based on a relative change value of the feature extracted at the extraction time, relative to a reference value of the feature obtained a time of calibration, and estimate blood pressure based on the relative change value of the extracted feature and the acquired offset.

20 Claims, 13 Drawing Sheets

(56) References Cited

U.S. PATENT DOCUMENTS

| | | | | |
|---|---|---|---|---|
| 9,289,133 | B2* | 3/2016 | Cohen | A61B 5/02007 |
| 2008/0287812 | A1* | 11/2008 | Parlikar | A61B 5/029 |
| | | | | 600/485 |
| 2009/0150082 | A1 | 6/2009 | Kang et al. | |
| 2015/0057554 | A1* | 2/2015 | Watson | A61B 5/7246 |
| | | | | 600/485 |
| 2016/0081563 | A1* | 3/2016 | Wiard | A61B 5/029 |
| | | | | 600/485 |
| 2017/0360314 | A1 | 12/2017 | Proenca et al. | |
| 2017/0367659 | A1* | 12/2017 | Lading | A61B 5/725 |
| 2018/0020991 | A1 | 1/2018 | Aung et al. | |
| 2018/0085011 | A1* | 3/2018 | Ma | A61B 5/0225 |
| 2018/0125422 | A1 | 5/2018 | Jang et al. | |

FOREIGN PATENT DOCUMENTS

| | | |
|---|---|---|
| JP | 2018-508273 A | 3/2018 |
| KR | 10-2009-0061153 A | 6/2009 |
| KR | 10-2013-0107066 A | 10/2013 |
| KR | 10-2018-0050946 A | 5/2018 |
| KR | 10-2018-0077019 A | 7/2018 |
| WO | 2016138965 A1 | 9/2016 |

\* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2018-0096674, filed on Aug. 20, 2018, in the Korean Intellectual Property Office, the disclosure of which is herein incorporated by reference in its entirety.

BACKGROUND

1. Field

Apparatuses and methods consistent with example embodiments relate to estimating blood pressure, and more particularly, to estimating blood pressure based on a relative change of a cardiovascular feature.

2. Description of Related Art

Recently, active research has been conducted on Internet technology (IT)-medical convergence technology, which is a combination of IT technology and medical technology, due to the aging population structure, rapidly growing medical expenses, and the shortage of professional medical service personnel. The monitoring of the health status of the human body is not limited to the hospital, but is expanding to the field of mobile health care, which monitors the health status of users moving in everyday life, such as home and office. Archetypal examples of bio-signals indicating the individual's health status may include an electrocardiography (ECG) signal, a photoplethysmogram (PPG) signal, an electromyography (EMG) signal, and the like. Various bio-signal sensors are being developed to measure such signals in daily life. Particularly, in the case of a PPG sensor, it is possible to estimate blood pressure of a human body by analyzing pulse waveforms in which a cardiovascular status is reflected.

SUMMARY

According to an aspect of an example embodiment, there is provided an apparatus for estimating blood pressure, including: a bio-signal sensor configured to measure a bio-signal from a user; and a processor configured to extract a feature from the bio-signal at an extraction time, acquire an offset based on a relative change value of the feature extracted at the extraction time, with respect to a reference value of the feature obtained at a time of calibration, and estimate a blood pressure based on the relative change value of the extracted feature and the acquired offset.

The bio-signal may include at least one of a photoplethysmogram (PPG) signal, an electrocardiography (ECG) signal, an electromyography (EMG) signal, a seismocardiogram (SCG) signal, and a ballistocardiogram (BCG) signal.

The processor may be further configured to extract a cardiac output (CO) and a total peripheral resistance (TPR) from the bio-signal, as the feature.

The processor may be further configured to acquire, from the bio-signal, characteristic points comprising at least one of heart rate information, a shape of a waveform of the bio-signal, an area under the waveform, time and amplitude of a maximum point of the bio-signal, time and amplitude of a minimum point of the bio-signal, and amplitude and time of each of constituent pulse waveforms constituting the bio-signal, and extract the feature related to a pulse pressure based on the characteristic points.

The processor may be further configured to calculate a first change value by normalizing the extracted CO based on a reference CO obtained at the time of calibration and calculate a second change value by normalizing the extracted TPR based on a reference TPR obtained at the time of calibration.

The processor may be further configured to calculate a third change value based on the first change value and the second change value and acquire the offset by inputting at least one of the first, the second, and the third change values into an offset estimation model.

The processor may be further configured to determine at least one of the first, the second, and the third change values to be input to the offset estimation model according to a preset time criterion.

The processor may be further configured to calculate a fourth change value based on the first change value and a change in a heart rate obtained from the bio-signal, input the fourth change value into an offset estimation model, and acquire the offset based on an output result of the offset estimation model.

The processor may be further configured to calculate a third change value based on the first change value and the second change value, and acquire the offset by combining the third change value with the output result of the offset estimation model.

The processor may be further configured to apply a weight to the first change value and the second change value, combine the weighted first and second change values with the acquired offset to obtain a combination result, and estimate the blood pressure by applying a scaling factor to the combination result.

The scaling factor may be set based on at least one of a mean arterial pressure (MAP) at the time of calibration, a diastolic blood pressure (DBP) at the time of calibration, and a systolic blood pressure (SBP) at the time of calibration.

The processor may be further configured to independently estimate the MAP, the DBP, and the SBP by adjusting at least one of the weight, the scaling factor, the first change value, and the second change value.

The processor may be further configured to estimate an amount of change in the blood pressure based on the relative change value of the feature and the offset, and estimate the blood pressure using the estimated amount of change and a reference blood pressure obtained at the time of calibration.

According to an aspect of another example embodiment, there is provided a method of estimate blood pressure, the method including: measuring a bio-signal from a user; extracting a feature from the bio-signal at an extraction time; determining a change in a value of the feature that occurs during a time period between a calibration time of the bio-signal and the extraction time; acquiring an offset based on the change in the value of the feature; and estimating a blood pressure based on the change in the value of the feature and the offset.

The extracting the feature may include extracting a cardiac output (CO) and a total peripheral resistance (TPR) from the bio-signal, as the feature.

The extracting the feature may include acquiring, from the bio-signal, characteristic points comprising at least one of heart rate information, a shape of a waveform of the bio-signal, an area under the waveform of the bio-signal, time and amplitude of a maximum point of the bio-signal, time and amplitude of a minimum point of the bio-signal, and amplitude and time of each of constituent pulse waveforms constituting the bio-signal, and extracting the feature related to a pulse pressure based on the acquired characteristic points.

The determining the change in the value of the feature may include calculating a first change value by normalizing the extracted CO based on a reference CO obtained at the time of calibration and calculating a second change value by normalizing the extracted TPR based on a reference TPR obtained at the time of calibration.

The determining the change in the value of the feature further may include calculating a third change value based on the first change value and the second change value and the acquiring the offset comprises acquiring the offset by inputting the first, the second, and the third change values to an offset estimation model.

The determining the change in the value of the feature may further include calculating a fourth change value based on the first change value and a change in a heart rate obtained from the bio-signal, and the acquiring the offset comprises inputting the fourth change value into an offset estimation model and acquiring the offset based on an output result of the offset estimation model.

The determining the change in the value of the feature further comprises calculating a third change value based on the first change value and the second change value, and the acquiring the offset comprises acquiring the offset by combining the third change value with the output result of the offset estimation model.

The estimating the blood pressure may include applying a weight to the first change value and the second change value, combining the weighted first and second change values with the offset to obtain a combination result, and applying a scaling factor to the combination result.

The estimating the blood pressure may include estimating an amount of change in the blood pressure based on the change in the value of the feature and the offset, and estimating the blood pressure based on the amount of change and a reference blood pressure obtained at the time of calibration.

According to an aspect of another example embodiment, there is provided an apparatus for estimating blood pressure, the apparatus including: a bio-signal measurer configured to measure a bio-signal from a user; a communication interface configured to receive a pulse pressure of the user from a pulse pressure measurement apparatus; and a processor configured to extract a feature from the bio-signal, acquire an offset based on a relative change value of the received pulse pressure relative to a reference value of the pulse pressure a time of calibration, and estimate a blood pressure based on the relative change value of the feature and the offset.

The processor may be further configured to extract, as the feature, a cardiac output (CO) and a total peripheral resistance (TPR) from the bio-signal, calculate relative change values of the CO, the TPR, and the pulse pressure relative to the time of calibration by normalizing the CO, the TPR, and the pulse pressure, respectively, based on a reference CO, a reference TPR, and a reference pulse pressure which are obtained at the time of calibration.

The processor is configured to apply a weight to the change value of the CO and the change value of the TPR, combine the weighted changed values of the CO and the TPR with the offset to obtain a combination result, and estimate the blood pressure by applying a scaling factor to the combination result.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
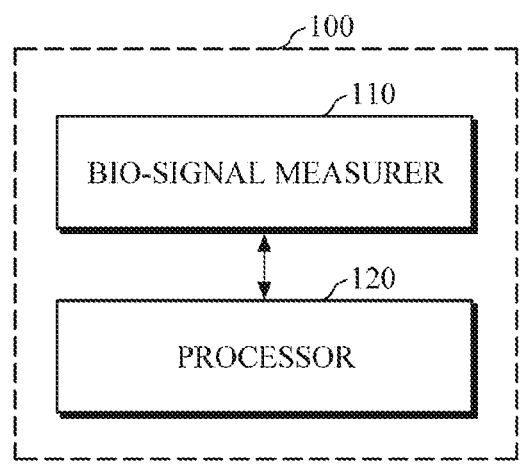
FIG. 1 is a block diagram illustrating an apparatus for estimating blood pressure according to one example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof. In addition, terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating blood pressure will be described in detail with reference to accompanying drawings.

FIG. 1 is a block diagram illustrating an apparatus for estimating blood pressure according to one embodiment. The apparatus 100 for estimating blood pressure may be mounted in a terminal, such as a smartphone, a tablet personal computer (PC), a desktop PC, a notebook PC, or the like, or may be manufactured as an independent hardware device. In this case, the independent hardware device may be a wearable device, such as a wristwatch type, a bracelet type, a wrist band type, a ring type, a glasses-type, or a hairband type, which can be worn on an object of interest. However, the apparatus 100 is not limited to the above examples.

Referring to FIG. 1, the apparatus 100 for estimating blood pressure may include a bio-signal measurer 110 and a processor 120.

The bio-signal measurer 110 may include one or more sensors and measure various bio-signals from an object of interest through the sensors. The bio-signal measurer 110 may measure a photoplethysmogram (PPG), an electrocardiography (ECG), a seismocardiogram (SCG), an electromyography (EMG), a ballistocardiogram (BCG), and a pulse pressure. Examples of the bio-signal measurer 110 may include a spectrometer, an optical sensor, a PPG sensor, an ECG sensor, a SCG sensor, an EMG sensor, a BCG sensor, and a pulse pressure sensor. However, the bio-signal measurer 110 is not limited to the above examples.

The processor 120 may control the bio-signal measurer 110 when a request for estimating blood pressure is received from a user or when a criterion for estimating blood pressure is satisfied. The processor 120 may receive a bio-signal from the bio-signal measurer 110 and estimate blood pressure based on the received bio-signal.

The processor 120 may extract features that may affect blood pressure from the bio-signal. Examples of the features may include cardiac output (CO) and total peripheral resistance (TPR).

For example, the processor 120 may acquire one or more characteristic points from the bio-signal and extract a feature for estimating blood pressure by combining the acquired characteristic points. In particular, the processor 120 may extract a one-period signal from the bio-signal continuously measured for a predetermined period of time. In addition, a representative waveform may be acquired from the extracted one-period signal and the characteristic points may be acquired using the acquired representative waveform. In this case, a feature may be extracted by combining one or more pieces of time information or amplitude information of the characteristic points.

When the feature is extracted from the bio-signal at the time of extraction, the processor 120 may estimate blood pressure using the extracted feature and a reference feature obtained at the time of calibration. For example, the processor 120 may estimate a relative change of the extracted feature relative to a reference value of the feature obtained at the time of calibration (e.g., a change in the extracted featured during a time period between the time of calibration and the time of extraction) and estimate blood pressure based on the relative change. The processor 120 may calculate a relative change value of the feature by normalizing the extracted feature based on the reference feature obtained at the time of calibration and estimate blood pressure using the calculated relative change value.

Meanwhile, since the CO and the TPR extracted from the bio-signal for estimating blood pressure are different from the actual CO and the actual TPR, the processor 120 may acquire an offset for correcting such a difference and reflect the acquired offset to the blood pressure estimation.

In one example, the processor 120 may acquire the offset by obtaining a first change value by normalizing the extracted CO based on a reference CO obtained at the time of calibration and obtaining a second change value by normalizing the extracted TPR based on a reference TPR obtained at the time of calibration. For example, a third change value may be calculated by multiplying the first change value by the second change value and the offset may be acquired by inputting the calculated third change value to an offset estimation model.

In another example, the processor 120 may acquire a feature related to pulse pressure other than the CO and the TPR and acquire the offset based on the feature related to the pulse pressure. The processor 120 may acquire a fourth change value based on a value obtained by normalizing the feature related to the pulse pressure based on a feature related to pulse pressure obtained at the time of calibration and acquire the offset by inputting the fourth change value to the offset estimation model.

In addition, the processor 120 may acquire, as a feature related to pulse pressure, an actual pulse pressure measured from the user through the pulse pressure sensor included in the bio-signal measurer 110 or an external pulse pressure estimation apparatus. Also, the processor 120 may extract a value corresponding to the pulse pressure or a heart rate as the feature related to the pulse pressure through pulse transit time (PTT), heart rate variability (HRV), peak amplitude analysis, or the like from the bio-signal.

The processor 120 may extract a CO feature and a TPR feature for each blood pressure from the bio-signal, acquire the offset for each blood pressure, or define a blood pressure estimation model for each blood pressure, thereby estimating each blood pressure independently.

Figure 2:
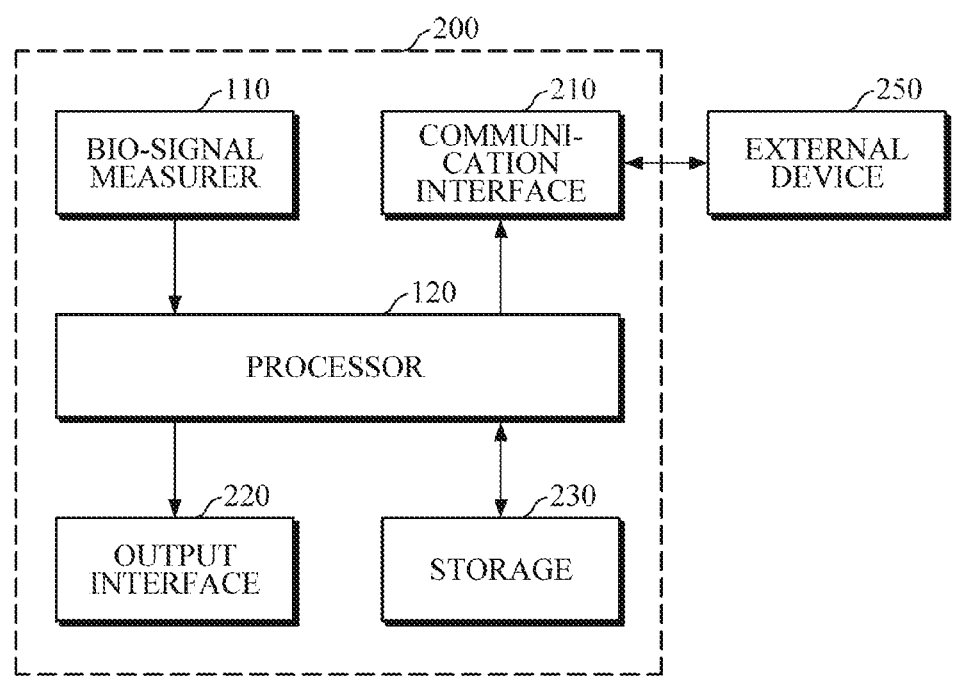
FIG. 2 is a block diagram illustrating an apparatus for estimating blood pressure according to another example embodiment.

FIG. 2 is a block diagram illustrating an apparatus for estimating blood pressure according to another example embodiment.

Referring to FIG. 2, the apparatus 200 for estimating blood pressure according to the present embodiment may include a bio-signal measurer 110, a processor 120, a communication interface 210, an output interface 220, and a storage 230.

The bio-signal measurer 110 may be electrically connected to the processor 120 and measure various bio-signals from a user under the control of the processor 120.

The processor 120 may receive a bio-signal from the bio-signal measurer 110 and extract, for example, a CO feature and a TPR feature for blood pressure estimation using the received bio-signal.

According to the present embodiment, the processor 120 may acquire additional information necessary for blood pressure estimation from an external device 250, in addition to the features extracted from the bio-signal. Examples of the external device 250 may include an external blood pressure measurement apparatus, an external pulse pressure apparatus, and other information processing apparatuses, such as a smartphone, a tablet personal computer (PC), a desktop PC, a notebook PC, and the like.

In one example, when the processor 120 receives a request for estimating blood pressure and a user is wearing or carrying an external pulse pressure measurement apparatus, the processor 120 may control the communication interface 210 to obtain a feature related to pulse pressure necessary for acquiring an offset. The communication interface 210 may communicate with the external pulse pressure measurement apparatus under the control of the processor 120 and directly receive pulse pressure information necessary for acquiring the offset from the external pulse pressure measurement apparatus. The request for estimating blood pressure may occur when there is a user's input or a predetermined criterion is satisfied. In this case, the predetermined criterion may be a predetermined measurement interval or a measurement time.

In another example, when the processor 120 receives a calibration request, the processor 120 may control the communication interface 210 to acquire reference information at the time of calibration. The communication interface 210 may be connected to an external blood pressure measurement apparatus and/or the external pulse pressure measurement apparatus under the control of the processor 120 and receive a reference blood pressure and/or a reference pulse pressure from the external blood pressure estimation apparatus and/or the external pulse pressure measurement apparatus. The calibration request may occur when there is a user's input or a calibration criterion is satisfied. Here, the calibration criterion may be set in advance as a predetermined interval, the total number of times when an estimated blood pressure deviates from a normal range, the number of consecutive times when the estimated blood pressure deviates from the normal range, or the like.

The communication interface 210 may access a communication network using a wired/wireless communication technology under the control of the processor 120. The communication interface 210 may transmit a processing result of the processor 120 to an external device 250. Examples of the communication technology may include Bluetooth communication, Bluetooth low energy (BLE) communication, near field communication (NFC), a wireless local area network (WLAN) communication, ZigBee communication, infrared data association (IrDA) communication, Wi-Fi direct (WFD) communication, ultra-wideband (UWB) communication, Ant+ communication, WiFi communication, radio frequency identification (RFID) communication, 3rd generation (3G) communication, 4G communication, 5G communication, etc. However, the communication technology is not limited to the above examples.

Meanwhile, the processor 120 may guide the user through the output interface 220 to measure blood pressure and/or pulse pressure using the external device 250 in response to the calibration request or the request for estimating blood pressure. The output interface 220 may output information for guiding the measurement of reference blood pressure and/or the measurement of pulse pressure using a visual output module, such as a display, a voice output module, such as a speaker, or a haptic module using vibration, tactile sensation, or the like, under the control of the processor 120. The processor 120 may output a user interface through the output interface 220. The user may use the user interface to input blood pressure and/or the pulse pressure measured through the external device 250.

The processor 120 may store, as reference information, a bio-signal measured through the bio-signal measurer 110 at the time of calibration, a feature extracted from the bio-signal, the blood pressure and/or the pulse pressure information measured through the external device 250 in the storage 230 for blood pressure estimation. In addition, the storage 230 may store a variety of other reference information, such as user characteristic information, such as user's age, sex, health condition, and the like, a blood pressure estimation model, an offset estimation model, and the like.

Examples of the storage 230 may include a storage medium, such as a memory of flash memory type, hard disk type, multimedia card micro type, or card type (e.g., SD or XD memory), random access memory (RAM), static random access memory (SRAM), read-only memory (ROM), electrically erasable programmable read-only memory (EE-PROM), programmable read-only memory (PROM), magnetic memory, magnetic disk, optical disk, or the like, but is not limited thereto.

The processor 120 may extract a feature from the bio-signal measured by the bio-signal measurer 110 in response to the request for estimating blood pressure and estimate blood pressure based on the reference information obtained at the time of calibration, which is stored in the storage 230. In particular, when the user's pulse pressure information is measured through the external pulse pressure measurement apparatus, the processor 120 may receive the measured pulse pressure information through the communication interface 210 or the interface of the output interface 220 and acquire an offset based on the received user's pulse pressure. The processor 120 may correct an error between a CO feature and a TPR feature, which are extracted from the bio-signal, and an actual CO and an actual TPR, using the acquired offset.

When the processor 120 completes the blood pressure estimation, the output interface 220 may output the bio-signal, the blood pressure estimation result, and additional information in accordance with the blood pressure estimation result. In one example, the output interface 220 may provide a variety of information visually through a display module. For example, when estimated blood pressure deviates from a normal range, the blood pressure result may be emphasized in red color, thereby presenting warning information to the user. In another example, a variety of information may be provided to the user through a speaker or a haptic module in a non-visual manner, such as a voice, vibration, tactile sensation, or the like. For example, systolic blood pressure (SBP) and diastolic blood pressure (DBP) may be informed by voice. When estimated blood pressure deviates from a predetermined normal range, the user may be informed of abnormality in health condition through vibration or tactile sensation.

When the processor 120 completes the blood pressure estimation, the storage 230 may store the bio-signal and/or the blood pressure estimation result.

Figure 3A:
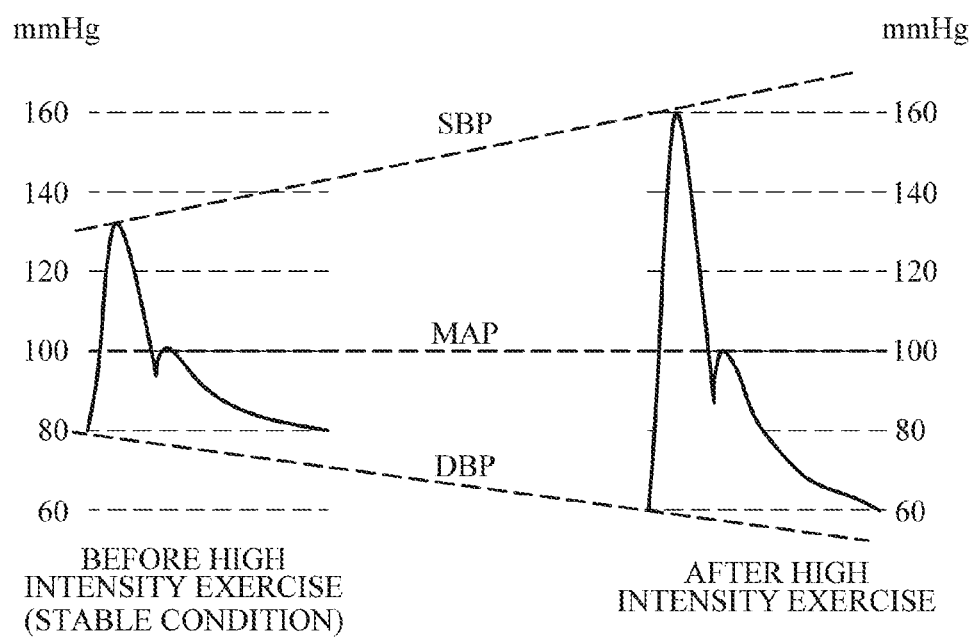
FIGS. 3A, 3B, and 3C are graphs for describing an offset estimation model.
Figure 3B:
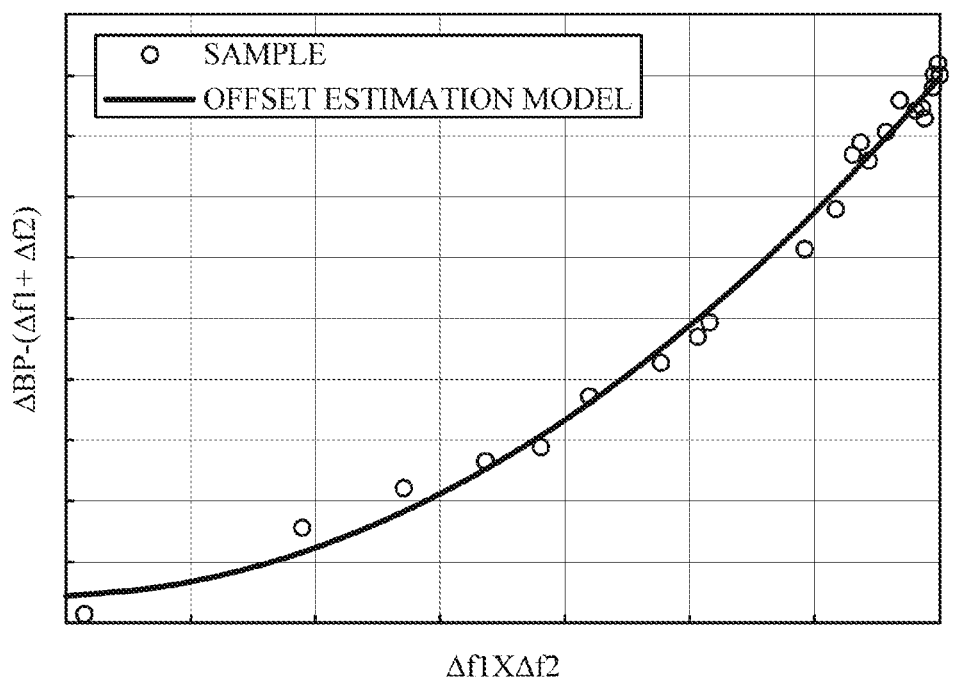
Figure 3C:
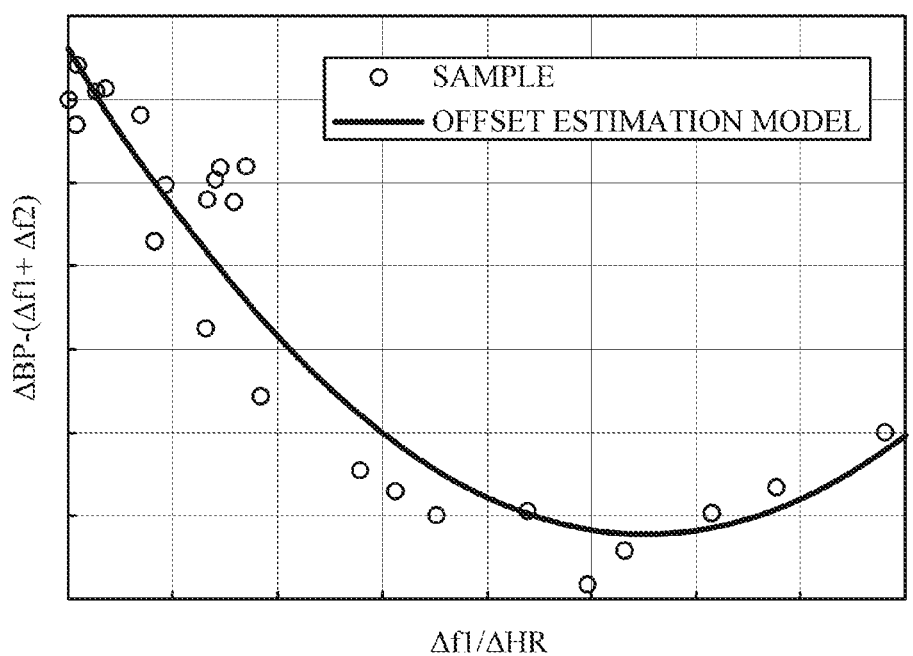

FIGS. 3A to 3C are graphs for describing an offset estimation model.

Generally, an amount of change in mean arterial pressure (MAP) is proportional to the CO and the TPR as shown in Equation 1 below.

$$\Delta MAP = CO \times TPR \tag{1}$$

Here, ΔMAP denotes a difference in MAP between the left ventricle and the right ventricle. Generally, mean right ventricular pressure does not exceed 3 to 5 mmHg and is similar to mean left ventricular pressure or brachial mean arterial pressure. Thus, when absolute CO and TPR values are known, it is possible to obtain the MAP in the aorta or an upper arm. However, it is difficult to estimate the absolute CO and TPR values based on the bio-signal.

In general, values within a range of plus or minus 0.5 to 0.7 of the MAP from the MAP calculated as described above may be used as SBP and DBP. However, a decoupling phenomenon may occur in which SBP and DBP do not follow the tendency of change of MAP according to a mechanism of blood pressure change. In addition, in a case of, for example, a high intensity aerobic exercise, in which the CO or the TPR changes significantly relative to a stable condition, an error of estimated blood pressure may be greatly increased.

For example, as shown in FIG. 3A, in various mechanisms of blood pressure change, the MAP may remain the same while DBP and SBP may change. This indicates a case in which the DBP and the SBP change according to the change in pulse pressure even when the MAP does not change.

According to the present embodiment, blood pressure may be estimated based on relative changes in CO and TPR features relative to the time of calibration. Since the pulse pressure may be determined based on changes in arterial stiffness and stroke volume (SV), an offset for correcting the error due to the amount of change in pulse pressure may be acquired using features related to the arterial stiffness and stroke volume and the obtained offset may be used in blood pressure estimation, thereby improving the accuracy.

FIGS. 3B and 3C are graphs for describing an offset estimation model. The offset estimation model may be in the form of a quadratic function as shown in Equation 2 below. However, the offset estimation model is not limited thereto, and may be a linear function, a piecewise linear function, a multi-dimension nonlinear function, or the like.

$$Y(X)=aX^2+bX+c \quad (2)$$

Here, X denotes an input value and Y(X) denotes an offset for input X. In addition, a, b, and c are predetermined constants, which are obtained through preprocessing as described with reference to FIGS. 3B and 3C. That is, input X of the offset estimation model may be defined variously as one of or a combination of two or more change values described above.

FIG. 3B shows an example in which an offset estimation model for acquiring an offset is derived using a third change value $\Delta f1 \times \Delta f2$ calculated based on a first change value $\Delta f1$ and a second change value $\Delta f2$. The first change value $M1$ may be obtained by normalizing an extracted CO by a reference CO, and the second change value $\Delta f2$ may be obtained by normalizing an extracted TPR by a reference TPR. The offset estimation model may be derived by acquiring coefficients a, b, and c thereof using a third change value $\Delta f1 \times \Delta f2$ and an optimal offset value $\Delta BP-(\Delta f1+\Delta f2)$ of each sample at a plurality of measurement times. Here, $\Delta BP$ represents the actual amount of change in blood pressure.

FIG. 3C is a graph showing an example in which an offset estimation model for acquiring an offset is derived based on a fourth change value related to pulse pressure. Coefficients a, b, and c of an offset estimation model are acquired using a fourth change value $\Delta f1/\Delta HR$ and an optimal offset value $\Delta BP-(\Delta f1+\Delta f2)$ at each point in time and the offset estimation model may be derived, wherein the fourth change value $\Delta f1/\Delta HR$ is calculated based on a value $\Delta HR$ obtained by normalizing heart rates of each sample obtained at a plurality of measurement times and a first change value $\Delta f1$.

Figure 4A:
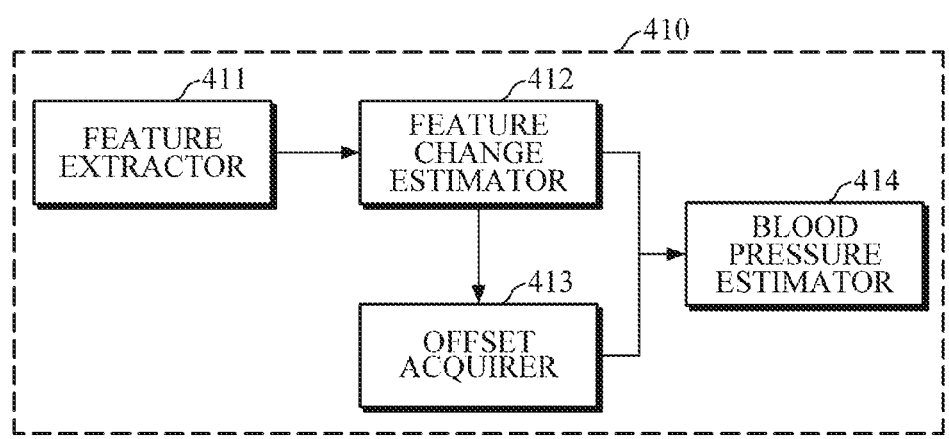
FIGS. 4A and 4B are block diagrams illustrating example embodiments of a configuration of the processor according to the example embodiments of FIGS. 1 and 2.
Figure 4B:
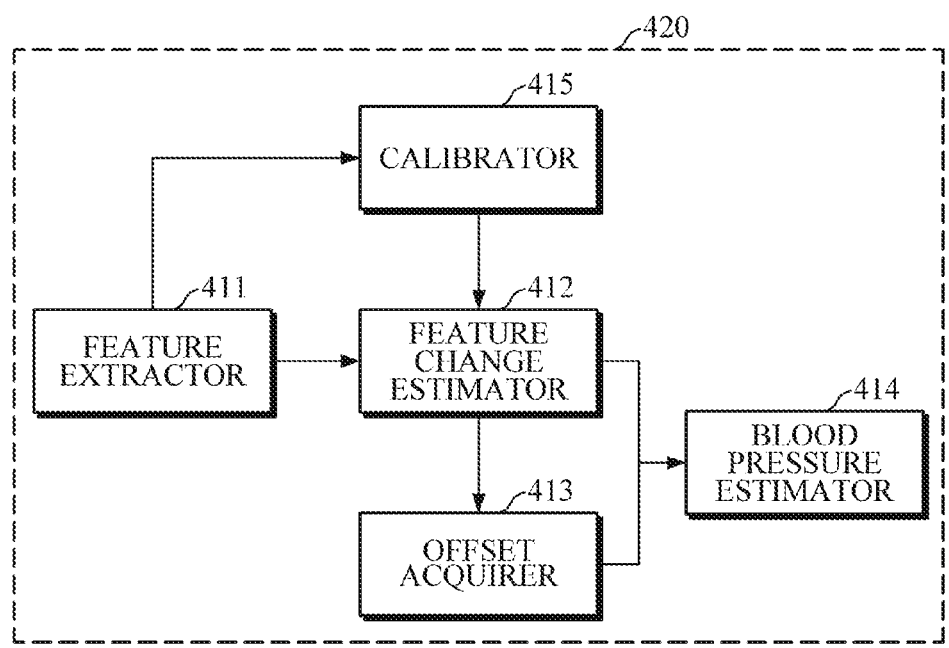
Figure 5A:
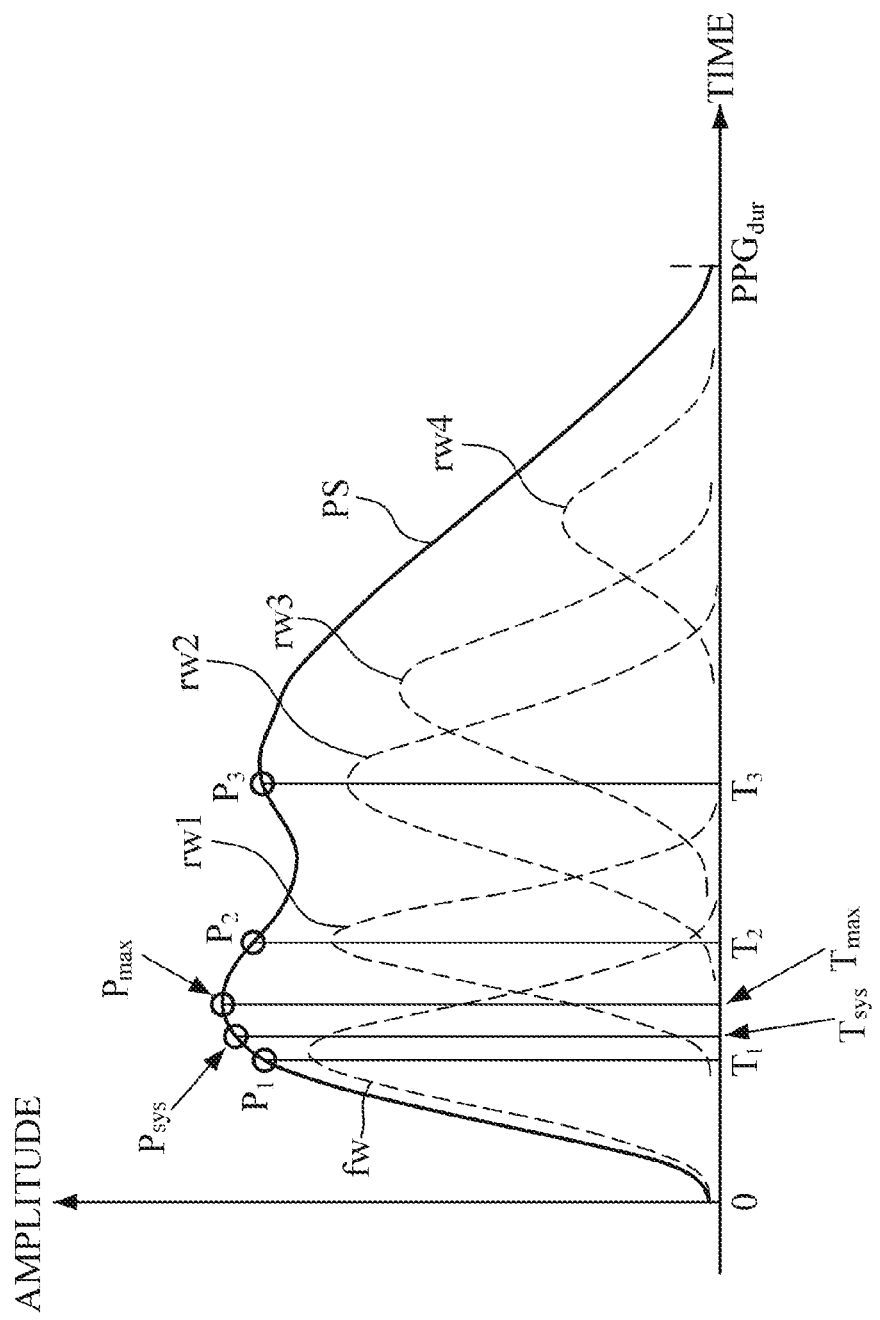
FIGS. 5A and 5B are graphs for describing feature extraction.

FIGS. 4A and 4B are block diagrams illustrating a configuration of the processor according to the embodiments of FIGS. 1 and 2. FIG. 5A is a diagram for describing extraction of a feature for blood pressure estimation. Embodiments of blood pressure estimation performed by the processors 410 and 420 will be described with reference to FIGS. 4A and 4B.

Referring to FIG. 4A, the processor 410 may include a feature extractor 411, a feature change estimator 412, an offset acquirer 413, and a blood pressure estimator 414.

The feature extractor 411 may extract a cardiovascular feature from various bio-signals measured from a user. In this case, the cardiovascular feature may include a CO feature and a TPR feature.

For example, the feature extractor 411 may acquire heart-beat information, a shape of a waveform of a bio-signal, time and amplitude of a maximum point of the bio-signal, time and amplitude of a minimum point of the bio-signal, the area of the bio-signal waveform, elapsed time of the bio-signal, amplitude and time information of each constituent pulse of the bio-signal from the bio-signal, acquire characteristic point information, such as information on an internally dividing point between the pieces of acquired information, and extract a feature using the acquired characteristic point information.

FIG. 5A shows an example of a pulse wave signal among the bio-signals acquired from the user. One example in which the feature extractor 411 extracts a feature from the pulse wave signal will be described with reference to FIG. 5A.

In general, a pulse wave signal is a superposition of a propagation wave propagating from the heart to vascular bifurcations of a body and reflection waves returning from the vascular bifurcations. FIG. 5A illustrates that a waveform of a measured pulse wave signal PS is a superposition of five constituent pulses, for example, a propagation wave fw and reflection waves rw1, rw2, rw3, and rw4.

The feature extractor 411 may acquire characteristic points by analyzing waveforms of the constituent pulses fw, rw1, rw2, rw3, and rw4 from the pulse wave signal PS. The first three constituent pulses fw, rw1, and rw2, may be used to estimate blood pressure. Subsequent pulses may not be observed in some users, may be difficult to detect due to noise, or may often have low correlation with blood pressure estimation.

For example, times $T_1$, $T_2$, and $T_3$ and amplitudes $P_1$, $P_2$, and $P_3$ of maximum points of the first to third constituent pulse waveforms fw, rw1, and rw2 may be obtained as characteristic points. When a pulse wave signal PS is obtained, a second-order derivative of the obtained pulse wave signal PS is computed and the times $T_1$, $T_2$, and $T_3$ and amplitudes $P_1$, $P_2$, and $P_3$ of maximum points of the constituent pulse waveforms fw, rw1, and rw2 may be obtained using the obtained second-order derivative signal. For example, local minimum points are searched for in the second-order derivative signal to extract times $T_1$, $T_2$, and $T_3$ corresponding to the first to third local minimum points and the amplitudes $P_1$, $P_2$, and $P_3$ corresponding to the extracted times $T_1$, $T_2$, and $T_3$ may be extracted from the pulse wave signal PS. Here, the local minimum point refers to a specific point, observed in a segment of the second-order derivative signal, at which the signal stops falling and starts to rise again. That is, the local minimum point refers to a downward convex point. However, the embodiment is not limited thereto, such that local maximum points may be searched for in the second-order derivative signal to extract times and amplitudes. In this case, the local maximum point refers to a specific point, observed in a segment of the second-order derivative signal, at which the signal ceases to rise and starts to fall again. That is, the local maximum point refers to an upward convex point.

In another example, the feature extractor 411 may obtain time $T_{max}$ and amplitude $P_{max}$ at a point in a predetermined interval of the pulse wave signal PS at which the amplitude is maximum as the characteristic points. The predetermined interval may refer to an interval from the beginning of the pulse wave signal to a point where the dictoric notch (DN) occurs, which indicates a blood pressure systolic period.

In another example, the feature extractor 411 may obtain time duration $PPG_{dur}$ indicating the total measurement time of the bio-signal or the area $PPG_{area}$ under the bio-signal waveform as the characteristic points. In this case, the area $PPG_{area}$ under the bio-signal waveform may refer to the total area under the waveform of the bio-signal or the area under the waveform of the bio-signal corresponding to a predetermined proportion (e.g., 70%) of the entire time duration $PPG_{dur}$.

In still another example, the feature extractor 411 may extract an internally dividing point between two or more characteristic points as an additional characteristic point. Unstable waveforms of the pulse wave signal may be generated due to non-ideal environment, such as motion noise, sleep, and the like so that the characteristic points may be extracted from wrong positions. In this case, blood pressure measurement may be supplemented by utilizing an internally dividing point between the erroneously extracted characteristic points.

For example, when characteristic points $(T_1, P_1)$ and $(T_{max}, P_{max})$ are obtained from the blood pressure systolic period, it is possible to obtain an internally dividing point $(T_{sys}, P_{sys})$ between the two characteristic points $(T_1, P_1)$ and $(T_{max}, P_{max})$. In this case, weights are applied to time values $T_1$ and $T_{max}$ of the two characteristic points $(T_1, P_1)$ and $(T_{max}, P_{max})$, time $T_{sys}$ of the internally dividing point may be obtained using the weighed time values, and an amplitude $P_{sys}$ corresponding to the time $T_{sys}$ of the internally dividing point may be extracted. However, the embodiment is not limited thereto, such that, through the analysis of the obtained bio-signal waveform, an internally dividing point between characteristic points $(T_1, P_1)$ and $(T_2, P_2)$ related to the first and second constituent pulse waveforms fw and $rw_1$ may be obtained from the blood pressure systolic period and an internally dividing point between characteristic points $(T_3, P_3)$ and $(T_4, P_4)$ related to the third and fourth consistent pulse waveforms $rw_2$ and $rw_3$ from the blood pressure diastolic period may be obtained.

The feature extractor 411 may extract a CO feature and a TPR feature by combining the various characteristic points obtained from the bio-signal as described above. For example, features may be extracted by performing multiplication, division, addition, subtraction, or a combination thereof on the plurality of characteristic points. Alternatively, features may be extracted using a function that uses a result of performing multiplication, division, addition, subtraction, or a combination thereof on the plurality of characteristic points as an input value. Here, the function may be a linear function, a quadric function, another multi-dimensional function, a logarithmic function, or an exponential function. It is apparent that other types of function can be used. In another example, a feature may be extracted using a function that uses at least one characteristic point as an input value. However, the embodiment is not limited to the above examples.

Meanwhile, the CO feature and the TPR feature may be extracted by combining the characteristic points differently according to characteristics of the user. In addition, the CO feature and the TPR feature may be individually extracted for each type of blood pressure by combining the characteristic points according to the blood pressure to be extracted, for example, MBP, DBP, and SBP.

Figure 5B:
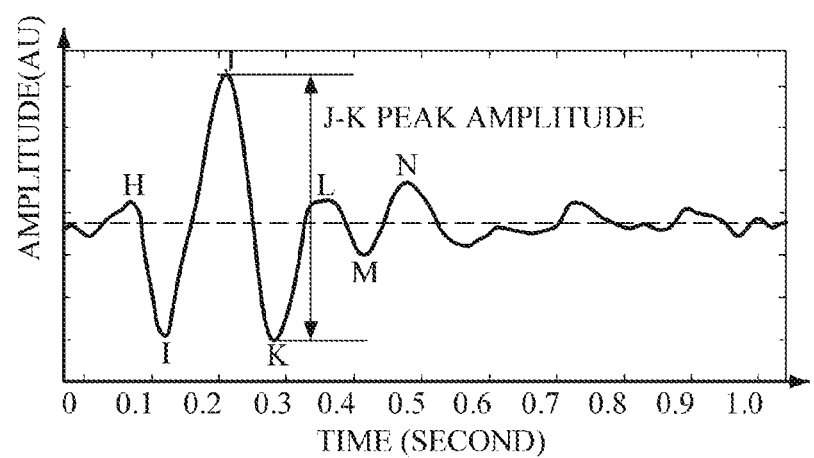

In addition, the feature extractor 411 may extract a feature related to pulse pressure from the measured bio-signal. For example, a heart rate (HR) may be extracted as a feature related to pulse pressure through an analysis of pulse transit time (PTT), heart rate variability (HRV), or the like of the measured bio-signal. In addition, as shown in FIG. 5B, estimated pulse pressure which is proportional to a J-K peak amplitude of a seismocardiogram (SCG) signal or a ballistocardiogram (BCG) signal may be extracted as a feature related to pulse pressure.

When the feature for blood pressure estimation is extracted, the feature change estimator 412 may estimate a relative change in the extracted feature using a reference feature obtained at the time of calibration. For example, the feature change estimator 412 may calculate a first change value by normalizing an amount of change in CO obtained at the time of blood pressure measurement relative to a reference CO obtained at the time of calibration to the reference CO. In addition, the feature change estimator 412 may calculate a second change value by normalizing an amount of change in TPR obtained at the time of blood pressure measurement relative to a reference TPR obtained at the time of calibration to the reference TPR.

Also, for each additional feature for offset acquisition, the feature change estimator 412 may calculate a relative change value relative to the time of calibration. In one example, the feature change estimator 412 may calculate a third change value by multiplying the first change value by the second change value. In another example, a fourth change value may be calculated by normalizing the feature related to pulse pressure to a feature related to pulse pressure obtained at the time of calibration. In this case, when the feature related to pulse pressure is an HR, the feature change estimator 412 may calculate a HR change value by normalizing the extracted HR to a reference HR obtained at the time of calibration and the calculate the fourth change value related to pulse pressure by dividing the first change value by the HR change value.

The offset acquirer 413 may acquire an offset by inputting the change value calculated for offset acquisition to an offset estimation model. In one example, the offset acquirer 413 may acquire an offset by inputting the third change value to the offset estimation model. In another example, one of the first to third change values is selected according to a predetermined criterion and the selected change value may be input to the offset estimation model. For example, a threshold may be set in advance for each change value, and a change value that exceeds the threshold or a change value that exceeds the threshold by the greatest amount may be determined to be input to the offset estimation model. However, the embodiment is not limited to the above examples.

In another example, an offset may be acquired by inputting the fourth change value related to pulse pressure to the offset estimation model. In another example, the fourth change value related to pulse pressure may be input to the offset estimation model and a final offset may be acquired by combining an output result of the offset estimation model with one of the first to third change values.

The offset estimation model may be defined in advance in consideration of the computing performance of the apparatus 100 for estimating blood pressure, a type of the bio-signal measurement sensor mounted in the apparatus 100, and various measurement conditions, such as user's characteristics. An input of the offset estimation model may be determined according to the offset estimation model applied to the apparatus 100.

The blood pressure estimator 414 may estimate an amount of change in blood pressure by inputting the first change value and the second change value estimated by the feature change estimator 412 and the offset acquired by the offset acquirer 413 to a blood pressure change estimation model. For example, one example of the blood pressure change estimation model is shown as Equation 3. Referring to Equation 3, the amount of change in blood pressure may be calculated by a linear combination of the first change value and the second change value with the offset. In this case, weights may be assigned to the first change value and the second change value and a scaling factor may be applied to a result of linear combination, so that the amount of change in blood pressure which reflects a characteristic of each user may be obtained.

$$\Delta BP = SF \times (\alpha \Delta f1 + \beta \Delta f2 + \text{Offset}) \tag{3}$$

Here, ΔBP denotes an estimated amount of change in blood pressure, and may be MAP, DBP, or SBP. Δf1 and Δf2 denote the first change value and the second change value, respectively. Offset denotes an offset acquired by the offset acquirer 413 using the offset estimation model shown in Equation 2. The variables α and β denote a weight assigned to each change value and may be defined according to a type of blood pressure to be estimated and/or the characteristics of the user. In addition, SF denotes a scaling factor which is defined adaptively according to the characteristics of the user and/or the type of blood pressure to be estimated. For example, the scaling factor may be reference MAP, reference DBP, or reference SBP, which is measured from the user by an external blood pressure measurement apparatus at the time of calibration, or a value calculated by combining two or more of the reference MAP, the reference DBP, and the reference SBP.

Meanwhile, the blood pressure estimator 414 may independently estimate the amount of change in MAP, DBP, and SBP using Equation 3 above. For example, a feature for estimating blood pressure may be extracted for each type of blood pressure and the amount of change in blood pressure of each type may be independently estimated. Alternatively, a weight and/or a scaling factor may be set differently for each type of blood pressure and the amount of change in blood pressure of each type may be independently estimated. For example, reference MAP of the user may be used as a scaling factor to estimate MAP. Similarly, reference DBP and reference SBP may be used as scaling factors to estimate DBP and SBP.

When the amount of change in blood pressure is estimated, the blood pressure estimator 414 may estimate blood pressure using a blood pressure estimation model as shown in Equation 4. Here, the blood pressure estimation model is illustrated as a linear combination, but is not limited thereto.

$$BP_{est} = BP_{cal} + \Delta BP \tag{4}$$

Here, $BP_{est}$ denotes estimated blood pressure, and ΔBP denotes an estimated amount of change in blood pressure. In addition, $BP_{cal}$ denotes reference blood pressure at the time of calibration. For example, estimated MAP may be calculated by inputting an amount of change in MAP and reference MAP to the blood pressure estimation model. Similarly, SBP and DBP are estimated in the same manner as the MAP, so that each type of blood pressure can be independently estimated.

In another example, the blood pressure estimator 414 may sequentially estimate MAP, DBP, and SBP. For example, the blood pressure estimator 414 may estimate MAP through the above Equations 3 and 4 and estimate DBP and SBP using the estimated MAP and pulse pressure. For example, when the feature related to pulse pressure is acquired as described above, the blood pressure estimator 414 may estimate DBP and SBP through Equations 5 and 6 below, which are examples of functions for estimating DBP and SBP.

$$DBP = MAP - \frac{PP}{3} \tag{5}$$

$$DBP = MAP - 0.01 \times \exp\left(4.14 - \frac{40.74}{HR}\right) \times PP$$

$$SBP = DBP + PP \tag{6}$$

Here, MAP denotes estimated mean arterial pressure, DBP denotes diastolic blood pressure, and SBP denotes systolic blood pressure. In addition, PP denotes pulse pressure, and HR denotes a heart rate.

Referring to FIG. 4B, the processor 420 may further include a calibrator 415 in addition to the configuration of the processor 410 shown in FIG. 4A.

When a calibration request of the user is received, or when whether calibration is required is determined by referring to preset calibration criteria as described above and the calibration is determined to be required, the calibrator 415 may perform calibration.

When performing calibration, the calibrator 415 may provide guidance for calibration to the user. For example, the calibrator 415 may guide the user to be in contact with the bio-signal measurer 110 to measure a reference bio-signal. In addition, the calibrator 415 may provide guidance about a time point of measurement of blood pressure, a measurement method, a communication connection between an external blood pressure measurement apparatus and the communication interface 310 so that the user measure the reference blood pressure through the external blood pressure measurement apparatus. In addition, when the user has the pulse pressure measurement apparatus separately the calibrator 415 may provide guidance about a time point of measurement of pulse pressure, a communication connection, and the like to measure pulse pressure through the external pulse pressure measurement apparatus.

When the reference blood pressure and/or reference pulse pressure are measured through the external blood pressure measurement apparatus and/or the external pulse pressure measurement apparatus, the calibrator 415 may acquire the reference blood pressure and/or the reference pulse pressure from the external blood pressure measurement apparatus and/or the external pulse pressure measurement apparatus. In particular, the reference blood pressure and/or the reference pulse pressure may be received directly through the communication connection with the communication interface 210 or from the user through a user interface.

When reference features, such as CO, TPR, a feature related to pulse pressure, and the like are extracted by the feature extractor 410, the calibrator 415 may receive the reference features from the feature extractor 410.

The calibrator 415 may store the acquired reference blood pressure, reference pulse pressure, reference features in the storage 230 as reference information for blood pressure measurement.

The calibrator 415 may calibrate an offset estimation model and/or a blood pressure estimation model based on the reference information. For example, the calibrator 415 may acquire the information, such as a reference bio-signal, the reference blood pressure, the reference pulse pressure, the reference features, and the like, at a plurality of points in time for a predetermined period of time and acquire a new coefficient of the offset estimation model using the method described with reference to FIGS. 3C and 3D, thereby calibrating the offset estimation model. Alternatively, the calibrator 415 may calibrate the blood pressure estimation model by applying newly acquired reference blood pressure for calibration to the blood pressure estimation model as shown in Equation 4.

Figure 6:
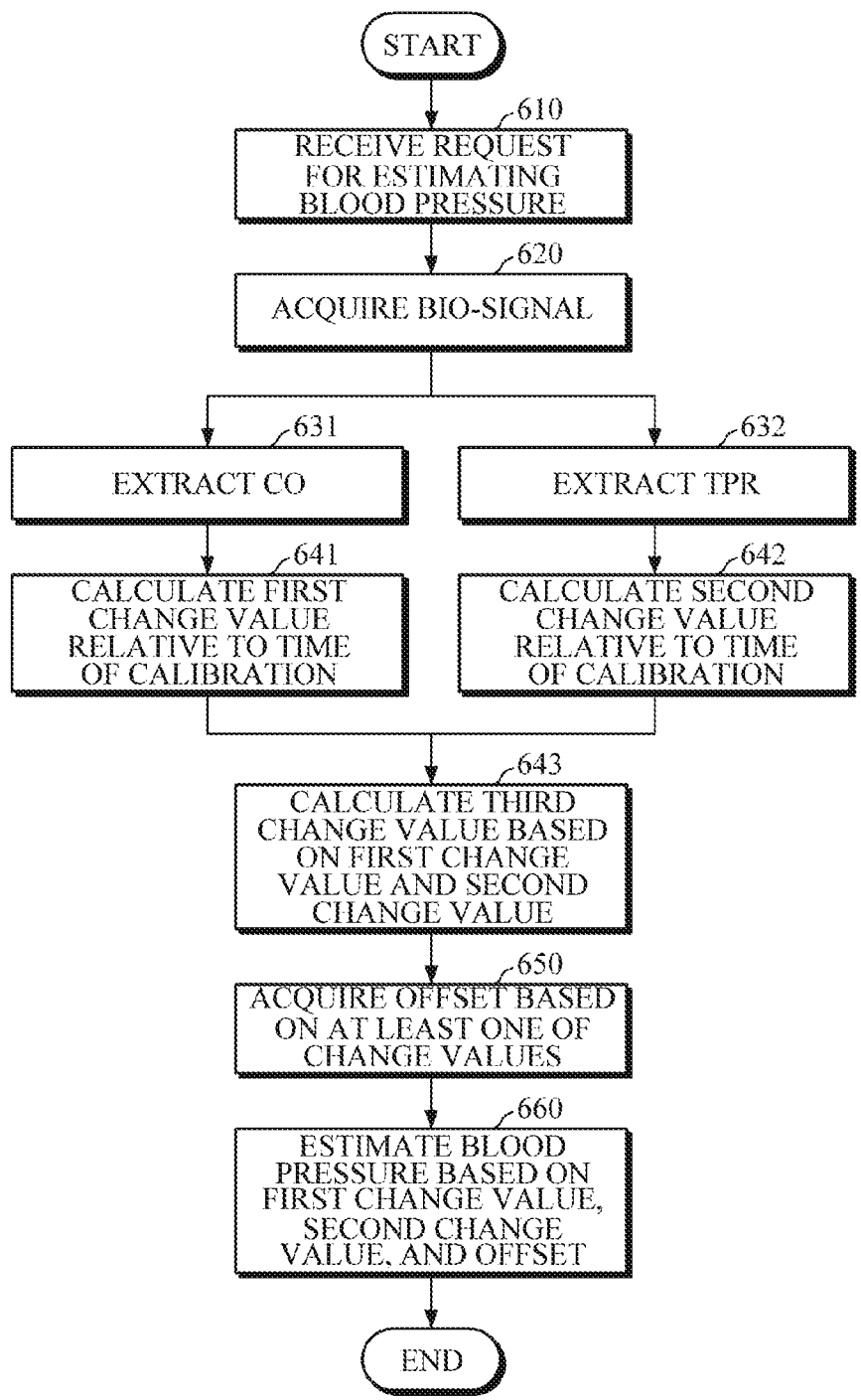
FIG. 6 is a flowchart illustrating a method of estimating blood pressure according to one example embodiment.

FIG. 6 is a flowchart illustrating a method of estimating blood pressure according to one example embodiment.

FIG. 6 is one embodiment of a method of estimating blood pressure in accordance with the embodiment of FIG. 1 or 2. Various embodiments are described in detail above, and hereinafter the method will be described in brief.

First, an apparatus 100/200 for estimating blood pressure may receive a request for estimating blood pressure in operation 610. The apparatus 100/200 may provide an interface to a user and receive the request for estimating blood pressure input by the user through the interface. Alternatively, the apparatus 100/200 may communicate with an external device and receive the request for estimating blood pressure from the external device. In this case, the external device may be a smartphone or a tablet PC carried by the user and the user may control an operation of the apparatus 100/200 for estimating blood pressure through the external device.

Then, the apparatus 100/200 for estimating blood pressure may acquire a bio-signal from the user by controlling a sensor (e.g., a bio-signal measurer 110) internally mounted for blood pressure estimation or receive a bio-signal from an external sensor in operation 620. The sensor mounted in the apparatus 100/200 and the external sensor may acquire various bio-signals, such as a PPG signal, an ECG signal, an EMG signal, an SCG signal, and a BCG signal, from various body parts (e.g., wrist, chest, fingers, etc.) of the user.

Then, the apparatus 100/200 may extract a CO feature and a TPR feature by analyzing the acquired bio-signal in operations 631 and 632. In particular, the apparatus 100/200 may acquire, form the bio-signal, characteristic points including information, such as heart rate information, a shape of a waveform of the bio-signal, time and amplitude of a maximum point of the bio-signal, time and amplitude of a minimum point of the bio-signal, the area of the bio-signal waveform, elapsed time of the bio-signal, and amplitude and time of each constituent pulse waveform of the bio-signal, and an internally dividing point between two or more characteristic points, and extract a cardiovascular feature by combining the pieces of acquired information.

A first change value that is a relative change of the CO feature relative to the time of calibration may be calculated in operation 641 and a second change value that is a relative change of the TPR feature relative to the time of calibration may be calculated in operation 642. For example, a relative amount of change in CO feature relative to reference CO obtained at the time of calibration may be normalized to the reference CO to calculate the first change value. Similarly, a relative amount of change in TPR feature relative to reference TPR obtained at the time of calibration may be normalized to calculate the second change value.

A third change value may be calculated based on the first change value and the second change value in operation 643.

An offset may be acquired by inputting the calculated third change value to the offset estimation model in operation 650. However, the embodiment is not limited thereto such that a change value satisfying predetermined criteria among the first change value, the second change value, and the third change value may be input to the offset estimation model.

Then, the apparatus 100/200 for estimating blood pressure may estimate blood pressure based on the first change value, the second change value, and the offset in operation 650. When blood pressure is estimated, the apparatus for estimating blood pressure may provide a blood pressure estimation result to the user.

Figure 7:
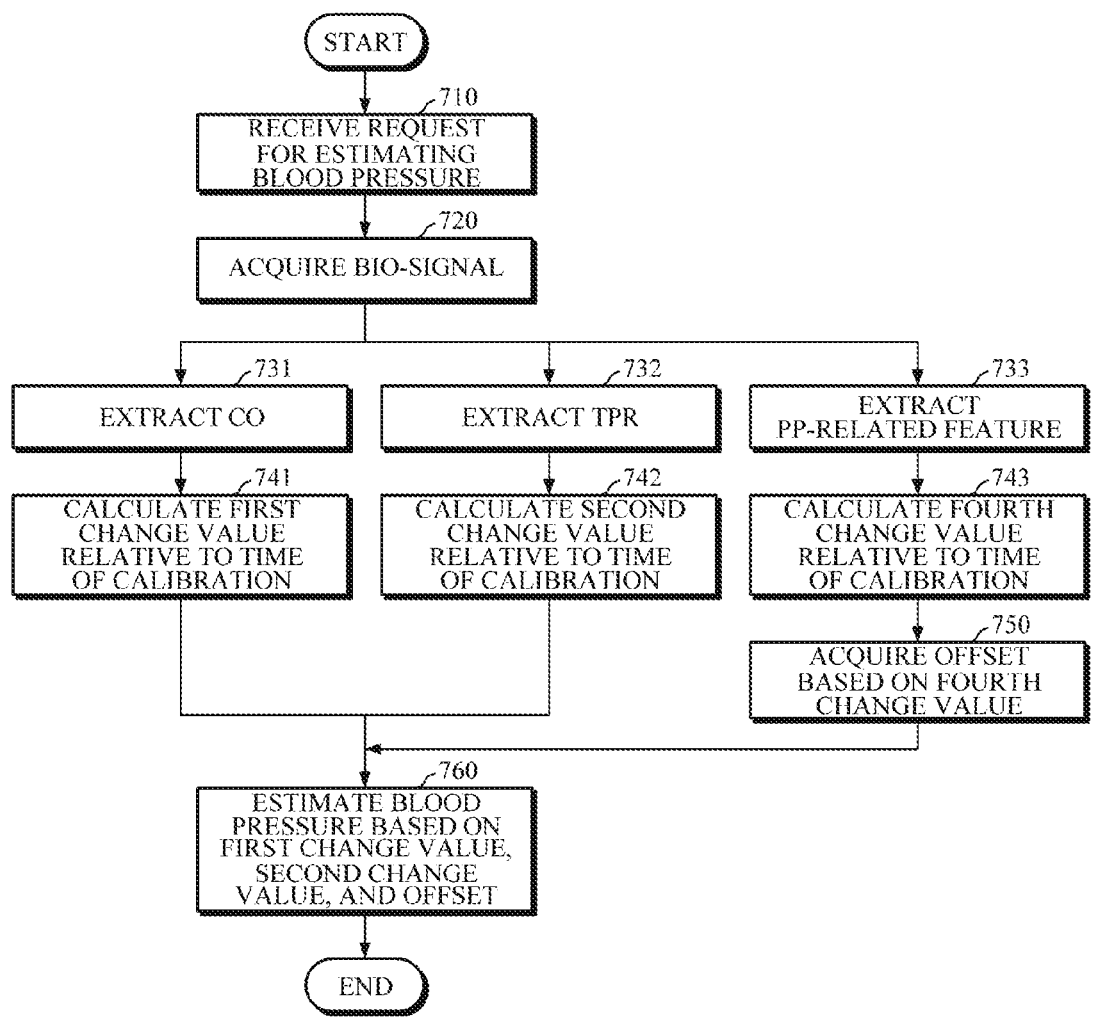
FIG. 7 is a flowchart illustrating a method of estimating blood pressure according to another example embodiment.

FIG. 7 is a flowchart illustrating another embodiment of the method of estimating blood pressure in accordance with the embodiment of FIG. 1 or 2. The method is described in detail above, and hence will be described below in brief.

First, the apparatus 100/200 for estimating blood pressure may receive a request for estimating blood pressure in operation 710 and acquire a bio-signal of a user in operation 720.

A CO feature may be extracted by analyzing the acquired bio-signal in operation 731 and a TPR feature may also be extracted in operation 732. In this case, one or more characteristic points are acquired from the bio-signal and the CO feature and the TPR feature may be extracted by combining the acquired characteristic points. In this case, each feature for estimating MAP, DBP, and SBP may be extracted by differently combining the characteristic points. In addition, a feature related to pulse pressure may be extracted for acquiring an offset in operation 733. In this case, the feature related to pulse pressure may include a heart rate.

a first change value that is a relative change of the CO feature relative to the time of calibration may be calculated in operation 741 and a second change value that is a relative change of the TPR feature relative to the time of calibration may be calculated in operation 724. In addition, a fourth change value may be calculated based on a relative change value of the pulse pressure-related feature relative to the time of calibration in operation 743. For example, when a heart rate is extracted as a relative change value of the pulse pressure-related feature, the fourth change value that corresponds to pulse pressure may be calculated by dividing the first change value by the relative change value of the heart rate. However, the embodiment is not limited to the above example, and when actual pulse pressure measured through an external pulse pressure measurement apparatus is input, the fourth change value may be calculated by normalizing the actual pulse pressure based on the pulse pressure obtained at the time of calibration.

An offset may be acquired by inputting the calculated fourth change value to an offset estimation model in operation 750. In this case, a third change value may be calculated based on the first change value and the second change value, and a final offset may be obtained by linearly combining the calculated third change value with an estimation result of the offset estimation model.

Then, the apparatus 100/200 for estimating blood pressure may estimate blood pressure based on the first change value, the second change value, and the offset in operation 760.

Figure 8A:
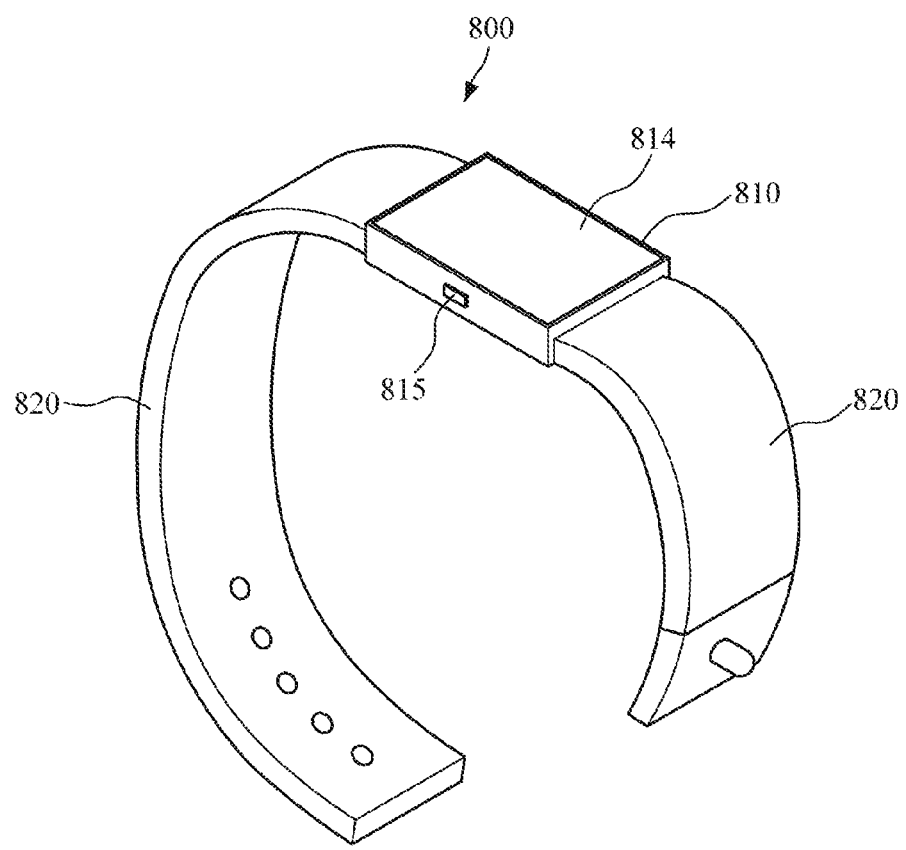
FIGS. 8A and 8B are diagrams for describing a wearable device according to one example embodiment.
Figure 8B:
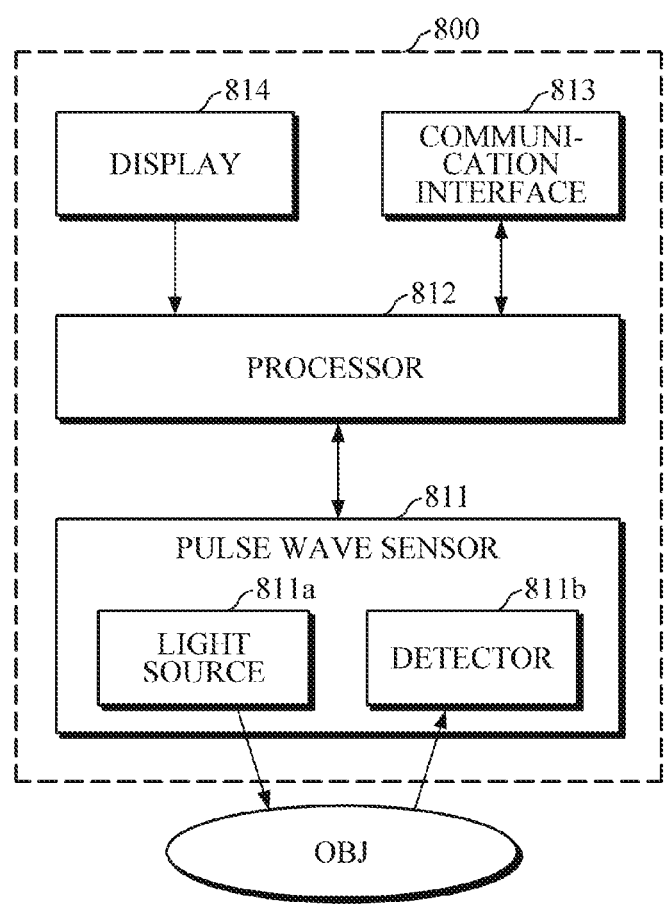

FIGS. 8A and 8B are diagrams for describing a wearable device according to one embodiment. The above-described various embodiments of the apparatus 100/200 for estimating blood pressure may be mounted in a smart watch worn on a wrist or a smart band type wearable device as shown in FIG. 8A. However, the embodiments are not limited thereto, and the apparatus 100/200 may be mounted in a device, such as a smartphone, a tablet PC, a desktop PC, a notebook PC, and the like.

Referring to FIGS. 8A and 8B, the wearable device 800 may include a main body 810 and a strap 820.

The strap 820 may be formed to be flexible so as to be bent in a shape to wrap around a wrist of a user or to be detached from the user's wrist. Alternatively, the strap 820 may be configured in the form of an undivided band. in this, the strap 820 may be filled with air or have an air bag to have elasticity according to a change in pressure applied to the wrist and may transmit the pressure change of the wrist to the main body 810.

A battery for supplying electric power to the wearable device may be embedded in the main body 810 or the strap 820.

In addition, one or more sensors for measuring various bio-signals may be mounted in the main body 810 which is brought into contact with an object OBJ (e.g., a wrist). For example, a pulse wave sensor 811 may be mounted on a rear surface of the main body 810, in such a manner that is exposed to the object OBJ. The pulse wave sensor 811 may include a light source 811*a* configured to emit light to the object OBJ and a detector 811*b* configured to measure a pulse wave signal by detecting light scattered or reflected from the object OBJ. In this case, the light source 811*a* may include at least one of a light emitting diode (LED), a laser diode, and a phosphor, and may be configured as a single array or two or more arrays.

The main body 810 of the wearable device 800 may include a processor 812 configured to estimate blood pressure based on the bio-signal received from the pulse wave sensor 811 and/or an external sensor. The processor 812 may control the pulse wave sensor 811 by generating a control signal in response to a user's request for estimating blood pressure, and, when necessary, control the communication interface 813 to receive the bio-signal from the external sensor.

The communication interface 813 may be mounted inside the main body 810 and communicate with the external device under the control of the processor 812 to transmit and receive necessary information. For example, the communication interface 813 may receive the bio-signal from an external sensor for measuring a bio-signal, for example, an ECG sensor, an EMG sensor, a BCG sensor, a pulse pressure sensor, and the like. In addition, the communication interface 813 may receive a request for estimating blood pressure from the user's mobile terminal. In addition, the communication interface 813 may cause the external device to estimate blood pressure by transmitting the extracted characteristic point or feature information to the external device. Also, the communication interface 813 may transmit a blood pressure estimation result to the external device such that the blood pressure estimation result can be displayed to the user or utilized for various purposes, such as blood pressure history management, disease research, and the like. Further, the communication interface 813 may receive a blood pressure estimation equation or reference information, such as reference blood pressure measured by a blood pressure measurement apparatus from the external device.

When the bio-signal is received from the pulse wave sensor 812 and/or the external sensor, the processor 812 may extract a CO feature and a TPR feature from the received bio-signal. For example, the above-described various characteristic points may be acquired by analyzing the pulse wave signal and the feature may be extracted by combining the acquired characteristic points. In this case, the processor 812 may extract the CO feature and the TPR feature for each of MAP, SBP, and DBP.

The processor 812 may estimate relative changes in CO feature and TPR feature relative to the time of calibration, taking into consideration difficulty in obtaining absolute values of the CO feature and the TPR feature, and estimate blood pressure using the estimated relative changes. In this case, in order to increase the accuracy of blood pressure estimation, the blood pressure may be estimated by reflecting a change in pulse pressure that affects the blood pressure.

For example, the processor 812 may acquire an offset that represents an effect due to the change in pulse pressure based on the relative changes in CO feature and TPR feature and apply the acquired offset to the blood pressure estimation. Alternatively, the processor 812 may extract a feature related to pulse pressure based on the pulse wave signal measured through the pulse wave sensor 811 or the signal received from the external sensor and acquire the offset using a relative change in the extracted feature related to pulse pressure relative to the time of calibration. In this case, the feature related to pulse pressure may include information about a heart rate or actual pulse pressure.

The wearable device 800 may further include an operator 815 and a display 814, which are mounted in the main body 810.

The operator 815 may receive a control command from the user and deliver the control command to the processor 812 and include a power button used for inputting a command for turning on/off the wearable device 800.

The display 814 may provide a variety of information related to the detected blood pressure to the user under the control of the processor 812. For example, the display 814 may provide additional information, such as detected blood pressure, alarm, warning, and the like, to the user in a visual/non-visual manner.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
   a bio-signal sensor configured to measure a bio-signal of a user; and
   a processor configured to:
   extract, from the bio-signal at an extraction time, at least two features including a cardiac output (CO) feature and a total peripheral resistance (TPR) feature;
   acquire an offset based on a multiplication of a CO feature change value of the CO feature extracted at the extraction time, with respect to a reference CO feature value obtained at a time of calibration, and a TPR feature change value of the TPR feature extracted at the extraction time, with respect to a reference TPR feature value obtained at the time of calibration; and
   estimate a blood pressure based on the CO feature change value, the TPR feature change value, and the offset, wherein the apparatus further comprises a memory configured to store an offset estimation model that indicates a relation between the offset and the multiplication of the CO feature change value and the TPR feature change value, and the processor is further configured to obtain the offset by inputting the CO feature change value and the TPR feature change value to the offset estimation model.

2. The apparatus of claim 1, wherein the bio-signal comprises at least one of a photoplethysmogram (PPG) signal, an electrocardiography (ECG) signal, an electromyography (EMG) signal, a seismocardiogram (SCG) signal, and a ballistocardiogram (BCG) signal.

3. The apparatus of claim 1, wherein the processor is further configured to acquire, from the bio-signal, characteristic points representing at least one of heart rate information, a shape of a waveform of the bio-signal, an area under the waveform, a time and an amplitude of a maximum point of the bio-signal, a time and an amplitude of a minimum point of the bio-signal, and an amplitude and a time of each of constituent pulse waveforms constituting the bio-signal, and extract the at least two features based on the characteristic points.

4. The apparatus of claim 1, wherein the processor is further configured to calculate the CO feature change value by normalizing the CO feature extracted at the extraction time based on the reference CO feature value obtained at the time of calibration and calculate the TPR feature change value by normalizing the TPR feature extracted at the extraction time based on the reference TPR feature value obtained at the time of calibration.

5. The apparatus of claim 4, wherein the processor is further configured to extract a heart rate (HR) feature from the bio-signal, and
wherein the processor is further configured to:
calculate a HR feature change value by normalizing the HR feature extracted at the extraction time, based on a reference HR feature value obtained at the time of calibration;
input the HR feature change value, the CO feature change value, and the TPR feature change value into the offset estimation model; and
acquire the offset based on an output result of the offset estimation model.

6. The apparatus of claim 5, wherein the processor is further configured to acquire the offset by combining the multiplication of the CO feature change value and the TPR feature change value with the output result of the offset estimation model.

7. The apparatus of claim 4, wherein the processor is further configured to apply a weight to the CO feature change value and the TPR feature change value, combine the weighted CO feature change value and the weighted TPR feature change value with the offset to obtain a combination result, and estimate the blood pressure by applying a scaling factor to the combination result.

8. The apparatus of claim 7, wherein the scaling factor is set based on at least one of a mean arterial pressure (MAP) at the time of calibration, a diastolic blood pressure (DBP) at the time of calibration, and a systolic blood pressure (SBP) at the time of calibration.

9. The apparatus of claim 8, wherein the processor is further configured to independently estimate the MAP, the DBP, and the SBP by adjusting at least one of the weight, the scaling factor, the CO feature change value, and the TPR feature change value.

10. The apparatus of claim 1, wherein the processor is further configured to estimate an amount of change in the blood pressure based on the CO feature change value, the TPR feature change value, and the offset, and estimate the blood pressure using the estimated amount of change and a reference blood pressure obtained at the time of calibration.

11. A method of estimating blood pressure, the method comprising:
measuring a bio-signal from a user;
extracting at least two features from the bio-signal at an extraction time, the at least two features including a cardiac output (CO) feature and a total peripheral resistance (TPR) feature;
acquiring an offset based on a multiplication of a CO feature change value of the CO feature extracted at the extraction time, with respect to a reference CO feature value obtained at a time of calibration, and a TPR feature change value of the TPR feature extracted at the extraction time, with respect to a reference TPR feature value obtained at the time of calibration; and
estimating a blood pressure based on the CO feature change value, the TPR feature change value, and the offset,
wherein the acquiring the offset comprises retrieving from a memory, an offset estimation model that indicates a relation between the offset and the multiplication of the CO feature change value and the TPR feature change value, and obtaining the offset by inputting the CO feature change value and the TPR feature change value to the offset estimation model.

12. The method of claim 11, wherein the extracting the at least two features comprises acquiring, from the bio-signal, characteristic points representing at least one of heart rate information, a shape of a waveform of the bio-signal, an area under the waveform of the bio-signal, a time and an amplitude of a maximum point of the bio-signal, a time and an amplitude of a minimum point of the bio-signal, and an amplitude and a time of each of constituent pulse waveforms constituting the bio-signal, and extracting the at least two features based on the acquired characteristic points.

13. The method of claim 11, wherein the acquiring the offset comprises:
calculating the CO feature by normalizing the CO feature extracted at the extraction time based on the reference CO feature value obtained at the time of calibration; and
calculating the TPR feature by normalizing TPR feature extracted at the extraction time based on the reference TPR feature value obtained at the time of calibration.

14. The method of claim 13, wherein the acquiring the offset comprises:
acquiring the offset by inputting the multiplication of the CO feature change value and the TPR feature change value to the offset estimation model.

15. The method of claim 13, further comprising extracting a heart rate (HR) feature from the bio-signal, and
wherein the acquiring the offset further comprises:
calculating a HR feature change value by normalizing the HR feature extracted at the extraction time, based on a reference HR feature value obtained at the time of calibration;
inputting the HR feature change value into the offset estimation model; and
acquiring the offset based on an output result of the offset estimation model.

16. The method of claim 15, wherein the acquiring the offset further comprises:

acquiring the offset by combining the multiplication of the CO feature change value and the TPR feature change value with the output result of the offset estimation model.

17. The method of claim 13, wherein the estimating the blood pressure comprises applying a weight to the CO feature change value and the TPR feature change value, combining the weighted CO feature change value and the weighted TPR feature value with the offset to obtain a combination result, and applying a scaling factor to the combination result.

18. The method of claim 11, wherein the estimating the blood pressure comprises estimating an amount of change in the blood pressure based on the CO feature change value, the TPR feature change value, and the offset, and estimating the blood pressure based on the amount of change and a reference blood pressure obtained at the time of calibration.

19. An apparatus for estimating blood pressure, the apparatus comprising:
a processor configured to:
receive a bio-signal of a user from an external pulse measurement device;
extract a cardiac output (CO) feature and a total peripheral resistance (TPR) feature from the bio-signal;
acquire an offset based on a multiplication of a CO feature change value of the CO feature extracted from the received bio-signal, with respect to a reference CO feature value obtained at a time of calibration, and a TPR feature change value of the TPR feature extracted from the received bio-signal, with respect to a reference TPR feature value obtained at the time of calibration; and
estimate a blood pressure based on the CO feature change value, the TPR feature change value and the offset,
wherein the apparatus further comprises a memory configured to store an offset estimation model that indicates a relation between the offset and the multiplication of the CO feature change value and the TPR feature change value, and the processor is further configured to obtain the offset by inputting the CO feature change value and the TPR feature change value to the offset estimation model.

20. The apparatus of claim 19, wherein the processor is further configured to:
apply a weight to the CO feature change value and the TPR feature change value to obtain a weighted CO feature change value and a weighted TPR feature change value;
combine the weighted CO feature change value and the weighted TPR feature change value with the offset to obtain a combination result; and
estimate the blood pressure by applying a scaling factor to the combination result.

* * * * *